United States Patent
Fredrickson et al.

(10) Patent No.: US 9,603,975 B2
(45) Date of Patent: Mar. 28, 2017

(54) BIOERODIBLE POLYMER COMPOSITIONS

(71) Applicant: Boston Scientific Scimed, Inc., Maple Grove, MN (US)

(72) Inventors: Gerald Fredrickson, Westford, MA (US); Michael David Sinisi, Boston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/971,430

(22) Filed: Dec. 16, 2015

(65) Prior Publication Data

US 2016/0166739 A1 Jun. 16, 2016

Related U.S. Application Data

(60) Provisional application No. 62/092,416, filed on Dec. 16, 2014.

(51) Int. Cl.
| | | |
|---|---|---|
| *C08G 63/02* | (2006.01) |
| *A61L 31/04* | (2006.01) |
| *A61L 31/14* | (2006.01) |
| *A61L 31/10* | (2006.01) |
| *C08G 63/12* | (2006.01) |
| *C08L 67/00* | (2006.01) |

(52) U.S. Cl.
CPC ............. *A61L 31/041* (2013.01); *A61L 31/10* (2013.01); *A61L 31/148* (2013.01); *C08G 63/12* (2013.01); *C08L 67/00* (2013.01)

(58) Field of Classification Search
CPC ................................ C08G 63/78; C08G 67/04
USPC ....... 528/271, 272; 514/10.1, 276, 279, 304, 514/330
See application file for complete search history.

(56) References Cited

U.S. PATENT DOCUMENTS

2002/0090398 A1* 7/2002 Dunn .................. A61K 9/0024
424/486

* cited by examiner

Primary Examiner — Terressa Boykin

(57) ABSTRACT

The present disclosure pertains to compositions that comprise (a) a bioerodible polyester network formed by reaction between reactive species that comprise a polyol and a polycarboxylate, wherein at least one of the polyol and polycarboxylate has a functionality of three or more, and (b) a bioerodible thermoplastic polymer. The present disclosure further pertains to methods of using such compositions and to medical devices that comprise such compositions.

20 Claims, 1 Drawing Sheet

BIOERODIBLE POLYMER COMPOSITIONS

STATEMENT OF RELATED APPLICATIONS

This application claims the benefit of U.S. Provisional Application Ser. No. 62/092,416, filed Dec. 16, 2014 and entitled "BIOERODIBLE POLYMER COMPOSITIONS", which is hereby incorporated by reference.

BACKGROUND

The present disclosure relates to bioerodible polymer compositions which, in various embodiments, are bioerodible elastomeric compositions. The bioerodible polymer compositions are useful, for example, in various medical applications including pharmaceutical and medical device applications.

SUMMARY

According to certain aspects, the present disclosure pertains to compositions that comprise (a) a bioerodible polyester network formed by reaction between reactive species that comprise a polyol and a polycarboxylate, wherein at least one of the polyol and polycarboxylate has a functionality of three or more, and (b) a bioerodible thermoplastic polymer.

In certain embodiments, (a) the polyol may be selected from a non-polymeric diol, a polymeric diol, a non-polymeric triol and a polymeric triol, (b) the polycarboxylate may be selected from a non-polymeric dicarboxylate, a polymeric dicarboxylate, a non-polymeric tricarboxylate, and a polymeric tricarboxylate, or (c) both (a) and (b). In certain embodiments, the polyol may comprise a triol, the polycarboxylate may comprise a tricarboxylate, or both. In certain embodiments, the polyol may comprise a polyester polyol (e.g., a polycaprolactone diol, a polycaprolactone triol, a combination thereof, etc.) and the polycarboxylate may comprise a non-polymeric tricarboxylate (e.g., citric acid, etc.).

In any of the above aspects and embodiments, the bioerodible thermoplastic polymer may have a melting point above body temperature, the bioerodible thermoplastic polymer may have a glass transition temperature below room temperature, or the bioerodible thermoplastic polymer may have both a melting point above body temperature and a glass transition temperature below room temperature.

In any of the above aspects and embodiments, the bioerodible thermoplastic polymer may be a bioerodible thermoplastic polyester.

In any of the above aspects and embodiments, the compositions may be solid compositions or the compositions may be liquid compositions.

Where the compositions are solid compositions, either the bioerodible polyester network may be covalently linked to the bioerodible thermoplastic polymer or the bioerodible polyester network may not be covalently linked to the bioerodible thermoplastic polymer. In either case, the bioerodible thermoplastic polyester may be covalently linked to itself, or the bioerodible thermoplastic polyester may not be covalently linked to itself. Due to the crosslinking that occurs, the solid compositions formed herein may not be thermoplastic compositions, even though they are formed by a reaction in which a bioerodible thermoplastic polymer is a reactant.

Where the compositions are liquid compositions, the bioerodible polyester network may be a partially crosslinked bioerodible polyester network (i.e., one in which unreacted carboxylic acid groups and alcohol groups remain for subsequent additional crosslinking). In some of these embodiments, the liquid compositions may further comprise a solvent within which the partially crosslinked bioerodible polyester network and the bioerodible thermoplastic polymer are dissolved or dispersed. Partial crosslinking, for example, allows the bioerodible polyester network to be dissolved or dispersed in a solvent. Partial crosslinking also allows for additional crosslinking in a subsequent step wherein a solid composition is formed, for example, a solid composition that is no longer dissolvable or dispersible in the solvent. In certain of these and other embodiments, the bioerodible thermoplastic polymer may be end capped with unsaturated groups and the liquid composition may further comprise a free radical initiator.

In some aspects, the present disclosure is directed to medical devices that comprise solid compositions according to any of the above aspects and embodiments. In some embodiments, the medical devices may be formed entirely of such solid compositions. In some embodiments, the medical devices may comprise a substrate and a coating disposed over at least a portion of the substrate, wherein the substrate, the coating, or both, may comprise such solid compositions.

In some aspects, the present disclosure is directed to methods that comprise heating liquid compositions according to any of the above aspects and embodiments, in order to further crosslink the partially crosslinked bioerodible polyester network. In some embodiments, such liquid compositions may be introduced to substrates, in which case the substrates may be, for example, molds into which such liquid compositions are introduced or medical device substrates onto which such liquid compositions may be introduced as a coating or covering. In these and other aspects and embodiments, the thermoplastic polymer may comprise unsaturated groups and the liquid composition may further comprises a free radical initiator, in which case the unsaturated groups may be crosslinked as a result of the heating or the unsaturated groups may be crosslinked upon application of ultraviolet light.

The present disclosure is advantageous in that compositions may be provided which are both elastomeric and bioerodible in certain embodiments. In the particular case of a stent, the fact that the covering material is elastomeric prevents cracking during implantation, aids in a stent's physical recovery (where self-expanding), and/or decreases the amount of time it takes for the stent to reach maximum expansion in vivo.

These and other aspects, embodiments and advantages of the present disclosure will become immediately apparent to those of ordinary skill in the art upon review of the detailed description and claims to follow.

DETAILED DESCRIPTION

Figure 1:
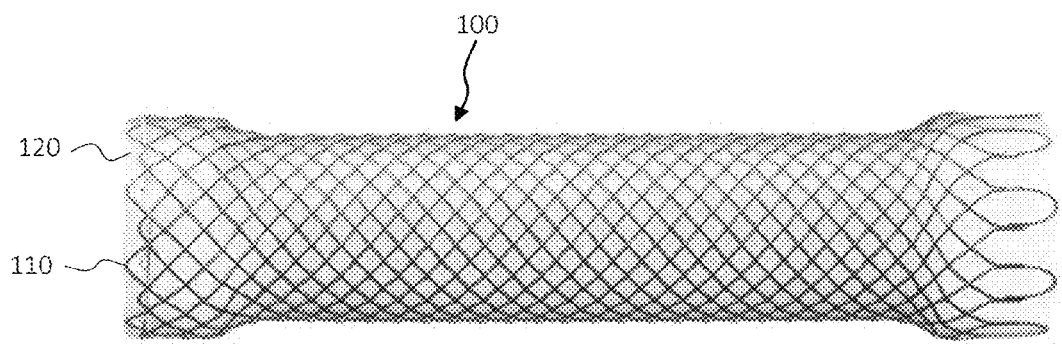
FIG. 1 is a schematic illustration of an esophageal stent, in accordance with an embodiment of the present disclosure.

The present disclosure relates to compositions that comprise (a) a bioerodible polyester network and (b) a bioerodible thermoplastic polymer, which may or may not be covalently linked to the bioerodible polymer network or to itself. The bioerodible polyester network may be formed, for example, by reaction between reactive species that include a polyol and a polycarboxylate, wherein at least one of the polyol and polycarboxylate has a functionality of three or more.

In this regard, a "functionality of three or more" refers to three or more carboxylic acid groups in a polycarboxylate and three or more alcohol groups in a polyol. As used herein, the term "carboxylate" includes carboxylic acids, carboxylic acid salts, carboxylic acid chlorides and carboxylic acid anhydrides.

The bioerodible polyester network and the bioerodible thermoplastic polymer in the compositions of the present disclosure are of different composition, for instance, differing in that a constitutional unit (i.e., a monomer) is found in bioerodible polyester network that is not found in the bioerodible thermoplastic polymer, in that a constitutional unit (i.e., a monomer) is found in the bioerodible thermoplastic polymer that is not found in the bioerodible polyester network, or a combination of both.

As used herein, the term "bioerodible" means capable of being degraded, dissolved, absorbed and/or otherwise disassembled, or digested by action of a biological environment. For an implantable medical device the biological environment is the position in the body where the medical device is configured to be implanted. For instance, for endoscopic stents such as esophageal, duodenal, biliary and colonic stents, the environment is the esophagus, duodenum, bile duct and colon, respectively; for a vascular stent, the environment is the vasculature; and so forth. As used herein a "thermoplastic polymer" is a polymer having a melting point above room temperature, typically above body temperature. As used herein an elastomeric sample is one which is able to undergo significant elongation at room temperature without yielding and with full recovery from the elongation.

The compositions described herein are useful in conjunction with pharmaceuticals and as well as a wide variety of medical devices, including entire medical devices and portions of medical devices, including medical device coatings and coverings.

In some embodiments, the compositions of the present disclosure are liquid compositions that comprise a bioerodible polyester network, a bioerodible thermoplastic polymer and a solvent. In these embodiments, the bioerodible polyester network is crosslinked, but only to a point where it can be dissolved or dispersed in a suitable solvent, along with the bioerodible thermoplastic polymer.

In some embodiments, the compositions of the present disclosure may be solid bioerodible polymer compositions that comprise a bioerodible polyester network and a bioerodible thermoplastic polymer. Such solid compositions are crosslinked to a greater extent than the liquid compositions described herein. Such solid compositions are bioerodible elastomeric compositions in various embodiments.

Figure 3:
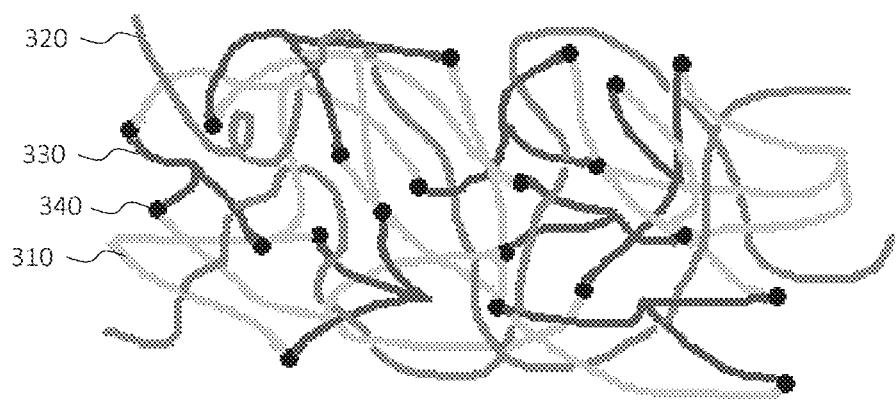
FIG. 3 is a schematic illustration of a semi-interpenetrating polymer network in accordance with an embodiment of the present disclosure.

In certain embodiments, the bioerodible thermoplastic polymer is not covalently coupled to the bioerodible polyester network or to itself. When the bioerodible thermoplastic polymer penetrates the bioerodible polyester network on a molecular scale, the resulting composition is sometimes referred to as a semi-interpenetrating network. FIG. 3 is a schematic illustration of such a semi-interpenetrating network wherein the dark gray lines 330 represent a polymeric polycarboxylate species and the light gray lines 310 represent a polymeric polyol, which form a crosslinked polyester network. The dots 340 represent the polyester crosslinks formed by the reaction between the carboxyl and hydroxyl groups. The lines of intermediate gray shade 320 represent a thermoplastic polymer that is not crosslinked within the matrix but is entangled in the crosslinked polyester network.

In certain embodiments of the compositions described herein, the bioerodible thermoplastic polymer is not covalently coupled to the bioerodible polyester network but is, however, crosslinked to itself, thereby forming a separate thermoplastic polymer network in which case the two networks may be at least partially interlaced on a molecular scale while not covalently bonded to each other. Such a composition, in which the polyester and thermoplastic polymer networks cannot be separated unless chemical bonds are broken, is sometimes referred to as an interpenetrating network.

Bioerodible polyester networks, which are crosslinked to varying degrees in the various embodiments of the present disclosure, may be formed from polycarboxylates and polyols.

Examples of polycarboxylates for use in the present disclosure (also referred to as polycarboxylic acids and polycarboxylated species) include non-polymeric and polymeric polycarboxylates.

Examples of non-polymeric polycarboxylates include non-polymeric dicarboxylates and tricarboxylates, for example, C2-C20 dicarboxylates and C3-C20 tricarboxylates. More specific examples of non-polymeric dicarboxylates and tricarboxylates include the following: oxalic acid, malonic acid, maleic acid, succinic acid, fumaric acid, malic acid, tartaric acid, glutaric acid, glutaconic acid, adipic acid, pimelic acid, cyclohexen-1,2-diacid, (o, m, or p)-phthalic acid, sebacic acid, suberic acid, hydroxyphthalic acid, citric acid, trimellitic acid, trimesic acid, aconitic acid, tricarballylic acid, ethanetricarboxylic acid.

Examples of polymeric polycarboxylates include dicarboxylated and tricarboxylated bioerodible polymers, which may be selected from dicarboxylated and tricarboxylated versions of the bioerodible polymers described elsewhere herein (e.g., as in conjunction with bioerodible polymers for use in forming substrates). Typically, the dicarboxylated and tricarboxylated bioerodible polymers will be of relatively low molecular weight, for example, being of 500 Daltons or less in number average molecular weight.

Examples of polyols (also referred to as polyalcohols, polyhydroxylated species, and polyhydroxylates) include non-polymeric and polymeric polyols.

Examples of non-polymeric polyols include non-polymeric diols and triols, for example, C2-C20 diols (e.g., α-ω, C2-C20) and C3-C20 triols. More specific examples of non-polymeric diols include 1,2 ethane diol, 1,4-butane diol, 1,6-hexane diol, 1,8-octane diol, 1,10-decane diol, and 1,12-dodecane diol, among others. More specific examples of non-polymeric triols include glycerol, trimethylolethane, trimethylolpropane, and trimethylolbutane, among others.

Examples of polymeric polyols include dihydroxylated and trihydroxylated bioerodible polymers, which may be selected from dihydroxylated and trihydroxylated versions of the bioerodible polymers described elsewhere herein. Typically, the dihydroxylated and trihydroxylated bioerodible polymers will be of relative low molecular weight, for example, being of 2000 Daltons or less in number average molecular weight. More specific examples of polymeric polyols include polycarprolactone diol, polycarprolactone triol, poly(ethylene oxide) diol, and poly(ethylene oxide) triol, among others. For example, two hydroxyl-terminated chains of polycaprolactone (i.e., polycaprolactone diol) may be formed from caprolactone using a diol (e.g., ethylene glycol) as an initiator. Similarly, three hydroxyl-terminated chains of polycaprolactone (i.e., polycaprolactone triol) may be formed from caprolactone using a triol (e.g., glycerol) as an initiator. Moreover, two hydroxyl-terminated chains of polyethylene oxide (i.e., polyethylene oxide diol) may be formed form ethylene oxide using a diol (e.g., ethylene glycol) as an initiator. Similarly, three hydroxyl-terminated chains of polyethylene oxide (i.e., polyethylene oxide triol) may be formed from ethylene oxide using a triol (e.g., glycerol) as an initiator.

In certain beneficial embodiments, the at least partially crosslinked bioerodible polyester network may be formed from reactants that comprise a non-polymeric polycarboxylate having a functionality of three and polymeric polyol selected from a polymeric polyol having a functionality of two, a polymeric polyol having a functionality of three, or both a polymeric polyol having a functionality of two and a polymeric polyol having a functionality of three. For instance, the at least partially crosslinked bioerodible polyester network may be formed from reactants comprising citric acid and a polycaprolactone polyol such as a polycaprolactone diol, a polycaprolactone diol, or both.

The stoichiometry of the reactive carboxylate groups and reactive alcohol groups may be varied from composition to composition. For example, the stoichiometry of the reactive carboxylate groups and reactive alcohol groups may be approximately equal (i.e., ranging from 0.9 to 0.95 to 1 to 1.05 to 1.1 moles (i.e., ranging between any two of the preceding values) of reactive carboxylate groups per one mole of reactive alcohol groups), there may be a stoichiometric excess of the reactive alcohol groups relative to the reactive carboxylate groups (e.g., ranging from 0.2 to 0.3 to 0.4 to 0.5 to 0.6 to 0.7 to 0.8 to 0.9 moles of reactive carboxylate groups per one mole of reactive alcohol groups), or there may be a stoichiometric excess of the reactive carboxylate groups relative to the reactive alcohol groups (e.g., ranging from 1.1 to 1.2 to 1.4 to 1.7 to 2 to 2.5 to 3.5 to 5 or more moles of reactive carboxylate groups per one mole of reactive alcohol groups).

As previously noted, in addition to an at least partially crosslinked bioerodible polyester network formed from polyols and polycarboxylates, the compositions of the present disclosure also comprise a bioerodible thermoplastic polymer.

The bioerodible thermoplastic polymer selected has a melting point above room temperature (25° C.), typically above body temperature (37° C.), more typically between 40° C. and 200° C., even more typically between 50° C. and 150° C. In certain beneficial embodiments, the bioerodible thermoplastic polymer will also have a glass transition temperature below body temperature, typically below room temperature, more typically between −150° C. and 20° C., more typically between −100° C. and 0° C. Glass transition temperature of a polymer is typically measured by differential scanning calorimetry (DSC) using the mid-point in the heat versus temperature transition as the Tg value. A typical heating rate for DSC measurement is 20° C./minute.

The addition of a bioerodible thermoplastic polymer to the compositions described herein is advantageous in that it enables the properties of the composition to be tailored to the particular application at hand. It can also be used to increase solution viscosity of various fluid compositions described herein.

Examples of bioerodible thermoplastic polymers include a wide variety of polyester and polyether homopolymers and copolymers, for example, from polyester homopolymers and copolymers comprising one or more of the following monomers, among others: glycolic acid (glycolide), D-lactic acid (D-lactide), L-lactic acid (L-lactide), D,L-lactic acid (D,L-lactide), ethylene oxide (ethylene glycol), caprolactone, valerolactone, p-dioxanone, butylene succinate, and hydroxybutyrate. Specific examples include, for instance, polyethylene oxide (also referred to as polyethylene glycol), polycaprolactone, poly(p-dioxanone), poly(butylene succinate), poly(lactic acid), poly(glycolic acid), and poly(lactic acid-co-glycolic acid).

In certain embodiments, the thermoplastic polymer is adapted to become covalently coupled to the polyester network, in which case the thermoplastic polymer preferably contains one or more hydroxyl groups, one or more carboxyl groups, or a combination of the same.

In certain embodiments, the thermoplastic polymer is adapted to not become covalently coupled to the polyester network or to itself, in which case the thermoplastic polymer may be provided with end groups that are non-reactive with carboxylate groups, hydroxyl groups or themselves.

In certain embodiments, the thermoplastic polymer is adapted to not become covalently coupled to the polyester network while also being adapted to crosslink to itself, in which case the thermoplastic polymer comprises two or more groups that are reactive with one another, but which are not reactive with hydroxyl or carboxylate groups. Examples of such groups include unsaturated groups, for examples, vinyl groups such as those associated with acrylates and methacrylates. In such embodiments, the composition may also optionally be provided with an additional species having multiple unsaturated groups such as vinyl groups, for example, non-polymeric diacrylates or triacrylates or low molecular weight (i.e., having a molecular weight less than 3000 Daltons) polymeric polyacrylates or polymethacrylates such as polymeric diacrylates, polymeric triacrylates, polymeric dimethacrylates, or polymeric trimethacrylates, among others.

Unsaturated groups can be reacted with one another via free radical polymerization. In these embodiments, compositions in accordance with the present disclosure may comprise a free radical initiator, examples of which include free-radical generating species that may be activated or accelerated by the application of heat (i.e., thermal initiators, such as peroxide initiators, azo initiators, etc.) and/or light (i.e., photoinitiators, such as riboflavin, 2-hydroxy-1-[4-(2-hydroxyethoxy) phenyl]-2-methyl-1-propanone (photoinitiator 2959), benzoin ethers, aryl ketones, acyl phosphine oxides, etc.).

In addition to the various species described above, the compositions of the present disclosure may also contain various supplemental agents, including therapeutic agents and imaging contrast agents. Examples of therapeutic agents and imaging contrast agents are described in more detail below. The compositions may comprise, for instance, from 0.1 wt % or less to 25 wt % or more of a therapeutic agent, for example, ranging from 0.1 to 0.25 to 0.5 to 1 to 2.5 to 5 to 10 to 25 wt % of a therapeutic agent. The compositions may comprise, for instance, from 0.1 wt % or less to 25 wt % or more of an imaging contrast agent, for example, ranging from 0.1 to 0.25 to 0.5 to 1 to 2.5 to 5 to 10 to 25 wt % of an imaging contrast agent.

Therapeutic agents include genetic therapeutic agents, non-genetic therapeutic agents and cells. Therapeutic agents may be used singly or in combination. Therapeutic agents may be, for example, nonionic or they may be anionic and/or cationic in nature.

Examples of therapeutic agents for use in connection with the present disclosure include: (a) anti-neoplastic/antiproliferative/anti-mitotic agents such as paclitaxel, Epo D, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (b) anti-thrombotic agents/anticoagulants such as heparin, heparin derivatives, urokinase, Ppack (dextrophenylalanine praline arginine chloromethylketone), D-Phe-Pro-Arg chloromethyl ketone, an RGD peptide-containing compound, hirudin, antithrombin compounds, platelet receptor antagonists, anti-thrombin antibodies, anti-platelet receptor antibodies, aspirin, cilostazole, thienopyridine (ticlopidine, clopidogrel), GP IIb/IIIa inhibitors such as abciximab, epitifibatide and tirofiban, prostaglandin inhibitors, platelet inhibitors and tick anti-platelet peptides; (c) radioisotopes (e.g., $^{90}$Y, $^{32}$P, $^{18}$F, $^{140}$La, $^{153}$Sm, $^{165}$Dy, $^{166}$Ho, $^{169}$Er, $^{169}$Yb, $^{177}$Lu, $^{186}$Re, $^{188}$Re, $^{103}$Pd, $^{198}$Au, $^{192}$Ir, $^{90}$Sr, $^{111}$In or $^{67}$Ga), which may be covalently bound or non-covalently bound to another species; (d) anti-inflammatory agents such as dexamethasone, prednisolone, corticosterone, budesonide, estrogen, sulfasalazine and mesalamine; (e) anesthetic agents such as lidocaine, bupivacaine and ropivacaine; vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin; (t) matrix deposition/organization pathway inhibitors such as halofuginone or other quinazolinone derivatives and tranilast; (u) analgesics including opioid analgesics, such as codeine, fentanyl, meperidine, methadone, morphine, pentazocine, and tramadol, and non-opioid analgesics, such as etodolac, fenoprofen, ketoprofen, ketorolac, mefenamic acid, paracetamol, and piroxicam, as well as non-steroidal anti-inflammatory drugs, such as aspirin, diclofenac, ibuprofen, indomethacin, and naproxen; (w) antispasmodic/anitcholinergic agents including oxybutynin (e.g., oxybutynin chloride), hyoscyamine (e.g., hyoscyamine sulfate) and flavoxate (e.g., flavoxate HCl); (v) local anesthetic agents including amino amides such as lidocaine, mepivacaine, prilocaine, bupivacaine, etidocaine, and dibucaine, and amino esters such as tetracaine, procaine, chloroprocaine, cocaine, and benzocaine; and (w) additional salts of the foregoing as well as combinations of the forgoing.

Non-invasive imaging is a valuable tool for use in conjunction with the compositions described herein. For example, imaging guidance, either internal or external, can be used to determine the location of the compositions. Consequently, compositions for use in connection with the present disclosure may also optionally include an effective amount of one or more imaging contrast agents (i.e., substances that enhance the image produced by medical diagnostic equipment). Currently available contrast agents include magnetic resonance imaging (MRI) contrast agents, ultrasonic imaging contrast agents, x-ray fluoroscopy contrast agents, nuclear medicine contrast agents, and others.

For example, x-ray based fluoroscopy is a diagnostic imaging technique that allows real-time patient monitoring of motion within a patient. To be fluoroscopically visible, compositions are typically rendered more absorptive of x-rays than the surrounding tissue (e.g., radiopaque materials). In various embodiments of the disclosure, this is accomplished by the use of contrast agents. Examples of contrast agents for use in connection with x-ray fluoroscopy include metals, metal salts and oxides (particularly bismuth salts and oxides), and iodinated compounds, among others. More specific examples of such contrast agents include tungsten, platinum, tantalum, iridium, gold, or other dense metal, barium sulfate, bismuth subcarbonate, bismuth trioxide, bismuth oxychloride, metrizamide, iopamidol, iothalamate sodium, iodomide sodium, and meglumine, among others.

Ultrasound uses high frequency sound waves to create an image of living tissue. A sound signal is sent out, and the reflected ultrasonic energy, or "echoes," are used to create the image. Ultrasound imaging contrast agents are materials that enhance the image produced by ultrasound equipment. Ultrasonic imaging contrast agents can be, for example, echogenic (i.e., materials that result in an increase in the reflected ultrasonic energy) or echolucent (i.e., materials that result in a decrease in the reflected ultrasonic energy). Suitable ultrasonic imaging contrast agents for use in connection with the present disclosure include solid particles ranging from about 0.01 to 50 microns in largest dimension (e.g., the diameter, where spherical particles are utilized), more typically about 0.5 to 20 microns. Both inorganic and organic particles can be used. Examples include microparticles/microspheres of calcium carbonate, hydroxyapatite, silica, poly(lactic acid), and poly(glycolic acid), among others. Microbubbles can also be used as ultrasonic imaging contrast agents, as is known in the imaging art.

Magnetic resonance imaging (MRI) produces images by differentiating detectable magnetic species in the portion of the body being imaged. In the case of $^1$H MRI, the detectable species are protons (hydrogen nuclei). In order to enhance the differentiation of detectable species in the area of interest from those in the surrounding environment, imaging contrast agents are often employed. These agents alter the magnetic environment of the detectable protons in the area of interest relative to that of protons in the surrounding environment and thereby allow for enhanced contrast and better images of the area of interest. For contrast-enhanced MRI, it is desirable that the contrast agent have a large magnetic moment, with a relatively long electronic relaxation time. Based upon these criteria, contrast agents such as Gd(III), Mn(II) and Fe(III) have been employed. Gadolinium(III) has the largest magnetic moment among these three and is, therefore, a widely-used paramagnetic species to enhance contrast in MRI. Chelates of paramagnetic ions such as Gd-DTPA (gadolinium ion chelated with the ligand diethylenetriaminepentaacetic acid) have been employed as MM contrast agents. Chelation of the gadolinium or other paramagnetic ion is believed to reduce the toxicity of the paramagnetic metal by rendering it more biocompatible, and can assist in localizing the distribution of the contrast agent to the area of interest.

Methods for forming compositions in accordance with the present disclosure will now be described.

As previously indicated, compositions in accordance with the present disclosure include fluid compositions, which may comprise a partially crosslinked bioerodible polyester network (e.g., formed from a partial reaction between a polyol and polycarboxylate) and a thermoplastic polymer, each dissolved or dispersed in a solvent. Concurrently or subsequent to solvent removal, the composition may be heated to react residual carboxylic acid groups and alcohol groups in the composition, thereby further crosslinking the compositions (e.g., until the composition is no longer dissolvable or dispersible in the solvent), thereby forming solid bioerodible polymer compositions, which may be solid bioerodible elastomeric compositions in some embodiments.

In certain embodiments, liquid compositions are formed using a polyester synthesis procedure wherein the following are reacted with one another: (a) a non-polymeric and/or polymeric polycarboxylate, which may be selected from those described above and (b) a polymeric and/or non-polymeric polyol, which may be selected from those described above. For example, the polycarboxylate species and polyol species may be combined in a suitable reaction vessel (e.g., a flask) with a suitable stirring mechanism (e.g., a stir bar) and brought to an elevated temperature that is sufficient to melt the polycarboxylate species and polyol species and to promote a condensation reaction between the polycarboxylate species and polyol species. During reaction, the mixture may be vigorously stirred under vacuum, with the vacuum pulling out the water generated from the reaction. Suitable reaction times and temperatures will vary depending on the reactants selected.

In various embodiments, the mixture is reacted to the point where a polyester network is formed that is not fully crosslinked (e.g., to the point where the composition comprises various branched polymers) so that it is still fluid and so that it can be dissolved or dispersed in a suitable solvent. Once this composition (also referred to as a prepolymer composition) is made and dissolved or dispersed in a suitable solvent for the composition, the selected thermoplastic polymer is also added to the solution or dispersion. Once the thermoplastic polymer is added, the entire mixture stirred until a fluid composition (e.g., a solution or dispersion) is made.

The solvent that is ultimately selected will contain one or more solvent species, which are generally selected based on their ability to dissolve or disperse the partially crosslinked polyester and thermoplastic polymer, in addition to other potential factors, including drying rate, surface tension, etc. In certain embodiments, the solvent is also selected based on its ability to dissolve or disperse supplemental agents, if any. Thus, optional supplemental agents, such as therapeutic agents or imaging contrast agents, may be dissolved or dispersed in the fluid composition. Examples of solvents include solvents formed from one or more of the following solvent species among others: ethyl acetate, isopropyl alcohol and xylene.

As previously indicated, one advantage of adding a thermoplastic polymer to the fluid compositions described herein is that it can act as a viscosity modifier, for example, increasing viscosity to improve processability in some embodiments. For example, by increasing viscosity, the compositions may more readily coat and remain in contact with a substrate. Depending on the functionality provided, the thermoplastic polymer will also react with or become entangled in the crosslinked network, in either case modifying the mechanical properties of the final product. For example, the thermoplastic polymer may increase elasticity of the final product or may effect bioerodibility. For instance, a more hydrophobic thermoplastic polymer such as polycaprolactone may promote a longer bioerosion time whereas a more hydrophilic thermoplastic polymer such as polyethylene oxide may decrease bioerosion times, for example, by virtue of acting as a conduit for moisture penetration.

Pharmaceutical formulations, medical devices and portions thereof may be formed from the fluid compositions described herein (which may also comprise supplemental agents such therapeutic agents, imaging contrast agents, etc.). In this regard, concurrently or subsequent to solvent removal, the composition may be heated to react residual carboxylic acid groups and alcohol groups in the composition, thereby further crosslinking the compositions (e.g., until the composition is no longer dissolvable or dispersible in the solvent) and forming solid bioerodible polymer compositions.

In some embodiments, fluid compositions may be applied to a substrate to form a solid bioerodible polymer composition. For example, the substrate may correspond to all or a portion of an implantable or insertable medical device to which the fluid compositions are applied, for example, by spraying, dipping, extrusion, and so forth. The substrate can also be, for example, a template, such as a mold, from which the bioerodible polymer composition is removed after solidification. In other embodiments, for example, extrusion and co-extrusion techniques, one or more solid bioerodible polymer compositions are formed without the aid of a substrate. Beneficial techniques include, for example, molding techniques, solvent casting techniques, spin coating techniques, web coating techniques, spraying techniques, dipping techniques, techniques involving coating via mechanical suspension including air suspension, ink jet techniques, electrostatic techniques, and combinations of these processes.

As previously noted, the bioerodible polymer compositions described herein may be used in conjunction with medical devices, for example, the bioerodible polymer compositions may be used to form entire medical devices or portions thereof, such as coatings, coverings or components for medical devices.

Specific examples of medical devices or the practice of the present disclosure include implantable or insertable medical devices, for example, stents (including esophageal stents, gastrointestinal stents, coronary vascular stents, peripheral vascular stents, cerebral stents, urethral stents, ureteral stents, biliary stents, and tracheal stents), stent coverings, stent grafts, vascular grafts, valves including heart valves and vascular valves, abdominal aortic aneurysm (AAA) devices (e.g., AAA stents, AAA grafts, etc.), vascular access ports, dialysis ports, embolization devices including cerebral aneurysm filler coils (including Guglilmi detachable coils and metal coils), embolic agents, tissue bulking devices, catheters (e.g., renal or vascular catheters such as balloon catheters and various central venous catheters), guide wires, balloons, filters (e.g., vena cava filters and mesh filters for distil protection devices), septal defect closure devices, myocardial plugs, patches, ventricular assist devices including left ventricular assist hearts and pumps, total artificial hearts, shunts, anastomosis clips and rings, band ligators, gastric bands, implantable electrical stimulation systems including neurostimulation systems such as spinal cord stimulation (SCS) systems, deep brain stimulation (DBS) systems, peripheral nerve stimulation (PNS) systems, gastric nerve stimulation systems, cochlear implant systems, and retinal implant systems, among others, cardiac systems including implantable pacemaker systems, implantable cardioverter-defibrillators (ICD's), and cardiac resynchronization and defibrillation (CRDT) devices, including polymeric components for leads including bioerodible lead coatings, and tissue engineering scaffolds for cartilage, bone, skin and other in vivo tissue regeneration (e.g., porous scaffolds, electrospun films and membranes for tissue integration), urethral slings, hernia "meshes", artificial ligaments, orthopedic prosthesis, one grafts, spinal disks, dental implants, biopsy devices, as well as any coated substrate (which can comprise, for example, metals, polymers, ceramics and combinations thereof) that is implanted or inserted into the body.

Materials for forming medical device substrates vary widely and thus include various organic materials (i.e., materials containing one or more types or organic species), such as polymers and various inorganic materials (i.e., materials containing one or more inorganic species), such as metallic materials (e.g., metals and metal alloys) and non-metallic materials (e.g., carbon, semiconductors, glasses, and ceramics containing various metal- and non-metal-oxides, various metal- and non-metal-nitrides, various metal- and non-metal-carbides, various metal- and non-metal-borides, various metal- and non-metal-phosphates, and various metal- and non-metal-sulfides, among others).

Specific examples of non-metallic inorganic materials may be selected, for example, from materials containing one or more of the following: metal-based ceramics including aluminum oxides and transition metal oxides (e.g., oxides of titanium, zirconium, hafnium, tantalum, molybdenum, tungsten, rhenium, and iridium); semi-metal-based ceramics, such as those containing silicon, silicon oxides (sometimes referred to as glass ceramics), germanium oxides, silicon and germanium nitrides, silicon and germanium carbides, calcium phosphate ceramics (e.g., hydroxyapatite); and carbon and carbon-based, ceramic-like materials such as carbon nitrides, among many others.

Specific examples of metallic inorganic materials may be selected, for example, from substantially pure metals (e.g., biostable metals such as gold, platinum, palladium, iridium, osmium, rhodium, titanium, tantalum, tungsten, and ruthenium, and bioerodible metals such as magnesium, zinc and iron), metal alloys comprising iron and chromium (e.g., stainless steels, including platinum-enriched radiopaque stainless steel), alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N) and alloys comprising cobalt, chromium, tungsten and nickel (e.g., L605), alloys comprising nickel and chromium (e.g., inconel alloys), and alloys comprising magnesium and/or iron. Further examples of metallic substrate materials include substantially pure bioerodible metals and bioerodible metal alloys whose main constituent is selected from alkali metals, alkaline earth metals, iron, and zinc, for example, metals and metal alloys containing magnesium, iron or zinc as a main constituent and one or more optional additional constituents selected from the following: alkali metals such as Li, alkaline-earth metals such as Ca and Mg, transition metals such as Mn, Co, Ni, Cr, Cu, Cd, Zr, Ag, Au, Pd, Pt, Re, Fe and Zn, Group Ma metals such as Al, and Group IVa elements such as C, Si, Sn and Pb.

Examples of polymeric substrate materials include a variety of biostable and bioerodible polymers. Examples of bioerodible polymers for use as substrates may be selected from suitable members of the following, among many others: (a) polyester homopolymers and copolymers such as polyglycolide (PGA), polylactide (PLA) including poly-L-lactide, poly-D-lactide and poly-D,L-lactide, poly(beta-hydroxybutyrate), poly-D-gluconate, poly-L-gluconate, poly-D,L-gluconate, poly(epsilon-caprolactone), poly(delta-valerolactone), poly(p-dioxanone), poly(trimethylene carbonate), poly(lactide-co-glycolide) (PLGA), poly(lactide-co-delta-valerolactone), poly(lactide-co-epsilon-caprolactone), poly(lactide-co-beta-malic acid), poly(lactide-co-trimethylene carbonate), poly(glycolide-co-trimethylene carbonate), poly(beta-hydroxybutyrate-co-beta-hydroxyvalerate), poly[1,3-bis(p-carboxyphenoxy)propane-co-sebacic acid], and poly(sebacic acid-co-fumaric acid), among others, (b) poly(ortho esters) such as those synthesized by copolymerization of various diketene acetals and diols, among others, (c) polyanhydrides such as poly(adipic anhydride), poly(suberic anhydride), poly(sebacic anhydride), poly(dodecanedioic anhydride), poly(maleic anhydride), poly[1,3-bis(p-carboxyphenoxy)methane anhydride], and poly[alpha,omega-bis(p-carboxyphenoxy)alkane anhydrides] such as poly[1,3-bis(p-carboxyphenoxy)propane anhydride] and poly[1,3-bis(p-carboxyphenoxy)hexane anhydride], among others; and (d) amino-acid-based polymers including tyrosine-based polyarylates (e.g., copolymers of a diphenol and a diacid linked by ester bonds, with diphenols selected, for instance, from ethyl, butyl, hexyl, octyl and benzyl esters of desaminotyrosyl-tyrosine and diacids selected, for instance, from succinic, glutaric, adipic, suberic and sebacic acid), tyrosine-based polycarbonates (e.g., copolymers formed by the condensation polymerization of phosgene and a diphenol selected, for instance, from ethyl, butyl, hexyl, octyl and benzyl esters of desaminotyrosyl-tyrosine), and tyrosine-, leucine- and lysine-based polyester-amides; specific examples of tyrosine-based polymers include includes polymers that are comprised of a combination of desaminotyrosyl tyrosine hexyl ester, desaminotyrosyl tyrosine, and various di-acids, for example, succinic acid and adipic acid, among others.

In a specific embodiment illustrated in FIG. 1, an endoscopic stent, specifically, an esophageal stent 100 is shown. The stent 100 comprises a stent substrate 110 in the form of one or more wires or filaments, which in an exemplary embodiment may be formed from a bioerodible material such as a bioerodible polymer (e.g., poly(lactide-co-glycolide) or a bioerodible metal (e.g., magnesium, iron, zinc, magnesium alloy, iron alloy, zinc alloy, etc.). The stent 100 shown also comprises a covering material 120 that may be formed from a bioerodible polymer composition, preferably a bioerodible elastomeric composition, in accordance with the present disclosure. Fully bioerodible stents of this type may be useful in the endoscopy field, as they allow for the healthcare provider to place stents without having to subsequently remove the stents in the case of benign tumors or prophylactic indications. A covering material on such stents is useful in resisting ingrowth associated with the medical condition for a predetermined time, after which the covering material and underlying stent substrate bioerode from the implantation site. The fact that the covering material is elastomeric prevents cracking during implantation, aids in a self-expanding stent's physical recovery, and decreases the amount of time it takes for the stent to reach maximum expansion in vivo.

Figure 2:
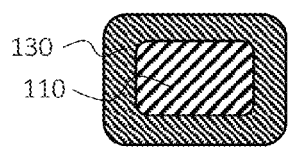
FIG. 2 is a schematic cross-sectional illustration of a coated strut of an esophageal stent, in accordance with an embodiment of the present disclosure.

In other embodiments, the bioerodible polymer composition may be in the form of a coating 130 on the stent substrate 110 as shown in cross section in FIG. 2, which leaves openings between the one or more wires or filaments making up the stent structural material 110.

Although various embodiments are specifically illustrated and described herein, it will be appreciated that modifications and variations of the present disclosure are covered by the above teachings and are within the purview of the appended claims without departing from the spirit and intended scope of the disclosure.

What is claimed is:

1. A composition comprising (a) a bioerodible polyester network formed by reaction between reactive species that comprise a polyol and a polycarboxylate, wherein at least one of the polyol and polycarboxylate has a functionality of three or more, and (b) a bioerodible thermoplastic polymer with a melting point above body temperature.

2. The composition of claim 1, wherein the polyol is selected from a non-polymeric diol, a polymeric diol, a non-polymeric triol, a polymeric triol, and wherein the polycarboxylate is selected from a non-polymeric dicarboxylate, a polymeric dicarboxylate, a non-polymeric tricarboxylate, and a polymeric tricarboxylate.

3. The composition of claim 1, wherein the reactive species comprise a triol, a tricarboxylate, or both.

4. The composition of claim 1, wherein the reactive species comprise (a) non-polymeric tricarboxylate and (b) a polyester polyol.

5. The composition of claim 1, wherein the reactive species comprise (a) citric acid and (b) a polycaprolactone diol, a polycaprolactone triol or both.

6. The composition of claim 1, wherein the bioerodible thermoplastic polymer has a glass transition temperature below room temperature.

7. The composition of claim 1, wherein the bioerodible thermoplastic polymer is a bioerodible thermoplastic polyester.

8. The composition of claim 1, wherein the composition is a solid composition.

9. The composition of claim 8, wherein the bioerodible polyester network is not covalently linked to the bioerodible thermoplastic polymer.

10. The composition of claim 9, wherein the bioerodible thermoplastic polymer is not covalently linked to itself or wherein the bioerodible thermoplastic polymer is covalently linked to itself.

11. The composition of claim 1, wherein the composition is a liquid composition and further comprises a solvent within which the bioerodible polyester network and the bioerodible thermoplastic polymer are dissolved or dispersed, wherein the bioerodible polyester network is a partially crosslinked bioerodible polyester network.

12. The composition of claim 11, wherein the bioerodible thermoplastic polymer is end capped with unsaturated groups and wherein the liquid composition further comprises a free radical initiator.

13. A method comprising (a) applying to a substrate a liquid composition comprising (i) a partially crosslinked bioerodible polyester network formed by reaction between reactive species that comprise a polyol and a polycarboxylate, wherein at least one of the polyol and polycarboxylate has a functionality of three or more, (ii) a bioerodible thermoplastic polymer and (iii) a solvent within which the partially crosslinked bioerodible polyester network and the bioerodible thermoplastic polymer are dissolved or dispersed and (b) heating the composition to further crosslink the partially crosslinked bioerodible polyester network.

14. The method of claim 13, wherein the substrate is a medical device substrate and wherein the liquid composition is applied as a coating or covering to the substrate.

15. The method of claim 13, wherein the bioerodible thermoplastic polymer comprises unsaturated groups and wherein the liquid composition comprises a free radical initiator that crosslinks the unsaturated groups as a result of the heating or that crosslinks the unsaturated groups upon application of ultraviolet light.

16. A method comprising (a) applying to a substrate a liquid composition comprising (i) a partially crosslinked biocompatible polyester network formed by reaction between reactive species that comprise a polyol and a polycarboxylate, wherein at least one of the polyol and polycarboxylate has a functionality of three or more, (ii) a biocompatible thermoplastic polymer and (iii) a solvent within which the partially crosslinked biocompatible polyester network and the biocompatible thermoplastic polymer are dissolved or dispersed and (b) heating the composition to further crosslink the partially crosslinked biocompatible polyester network.

17. The method of claim 16, wherein the substrate is a medical device substrate and wherein the liquid composition is applied as a coating or covering to the substrate.

18. The method of claim 16, wherein the biocompatible thermoplastic polymer comprises unsaturated groups and wherein the liquid composition comprises a free radical initiator that crosslinks the unsaturated groups as a result of the heating or that crosslinks the unsaturated groups upon application of ultraviolet light.

19. A method comprising (a) applying to a substrate a liquid composition comprising (i) a partially crosslinked bioerodible polyester network formed by reaction between reactive species that comprise a polyol and a polycarboxylate, wherein at least one of the polyol and polycarboxylate has a functionality of three or more, (ii) a biocompatible thermoplastic polymer and (iii) a solvent within which the partially crosslinked bioerodible polyester network and the biocompatible thermoplastic polymer are dissolved or dispersed and (b) heating the composition to further crosslink the partially crosslinked bioerodible polyester network.

20. The method of claim 19, wherein the substrate is a medical device substrate and wherein the liquid composition is applied as a coating or covering to the substrate.

* * * * *